US008889951B2

(12) United States Patent
Materne et al.

(10) Patent No.: US 8,889,951 B2
(45) Date of Patent: Nov. 18, 2014

(54) HERBICIDE RESISTANT BARLEY EXPRESSING MUTANT ACETOHYDROXY ACID SYNTHASE

(75) Inventors: Michael Materne, Horsham (AU); Christopher Pittock, Horsham (AU); David Moody, Horsham (AU)

(73) Assignee: Agriculture Victoria Services Pty Ltd, Attwood, Victoria (AU)

( * ) Notice: Subject to any disclaimer, the term of this patent is extended or adjusted under 35 U.S.C. 154(b) by 873 days.

(21) Appl. No.: 12/991,172

(22) PCT Filed: May 6, 2009

(86) PCT No.: PCT/AU2009/000558
§ 371 (c)(1),
(2), (4) Date: Jan. 28, 2011

(87) PCT Pub. No.: WO2009/135254
PCT Pub. Date: Nov. 12, 2009

(65) Prior Publication Data
US 2011/0126327 A1    May 26, 2011

(30) Foreign Application Priority Data

May 6, 2008   (AU) .............................. 2008902205

(51) Int. Cl.
*A01H 5/00* (2006.01)
*A01H 9/00* (2006.01)
*A01H 1/06* (2006.01)
*A01H 5/10* (2006.01)

(52) U.S. Cl.
CPC ... *A01H 1/06* (2013.01); *A01H 5/10* (2013.01)
USPC ............ 800/300; 800/320; 800/295; 800/298

(58) Field of Classification Search
None
See application file for complete search history.

(56) References Cited

U.S. PATENT DOCUMENTS

| | | | | |
|---|---|---|---|---|
| 2003/0236208 | A1* | 12/2003 | Kmiec et al. .................... | 514/44 |
| 2008/0234130 | A1* | 9/2008 | McCutchen et al. .......... | 504/128 |
| 2009/0205064 | A1 | 8/2009 | Schopke | |

FOREIGN PATENT DOCUMENTS

| | | |
|---|---|---|
| CN | 150226 A | 6/2004 |
| CN | 1946849 | 4/2007 |
| WO | WO2006/007373 A2 | 1/2006 |
| WO | WO2009046334 | 4/2009 |

OTHER PUBLICATIONS

Duggleby et al, Partial Sequence of Barley Acetohydroxyacid Synthase, Direct Submission to GenBank; Submitted Apr. 15, 1998; GenBank Accession No. AF059600.*
Mulholland et al, Effects of Soil Compaction on Barley (*Hordeum vulgare* L.) Growth I. Possible Role for ABA as a Root-Sourced Chemical Signal, J. of Exp. Botany (1996) 47:539-549.*
Siyuan Tan et al: "Imidazolinone-tolerant crops: history, current status and future", Pest Management Science, Wiley & Sons, Bognor Regis; GB, vol. 61, No. 3, Mar. 1, 2005, pp. 246-257, XP008154146, ISSN: 1526-498X, DOI: 10.1002/PS.993 [retrieved on Dec. 31, 2004].
Li, D. et al., A mutation at the Ala122 position of acetohydroxyacid synthase (AHAS) located on chromosome 6D of wheat: improved resistance to imidazolinone and a faster assay for marker assisted selection, Molecular Breeding, vol. 22, No. 2, Mar. 21, 2008, pp. 217-225, Klumer Academic Publishers, DO.
Rodriguez-Suarez, C. et al., Selection 1-11 and molecular characterization of imidazoline resistant mutation-derived lines of tritordeum HT621, Molecular Breeding, vol. 23, No. 4, Jan. 20, 2009, pp. 565-572, Klumer Academic Publishers, DO.
Lee Hyejin et al., Single Nucleotide mutation in the barley acetohydroxy acid synthase (AHAS) gene confers resistance to imidazolinone herbicides, Proceedings of the National Academy of Sciences of the United States of America vol. 108, No. 21, May 2011, (2011-2005).
Georg Jander, Scott R. Baerson, Jebecka A. Hudak, Kathleen A. Gonzalez, Kenneth J. Gruys and Robert L. Last; Ethylmethanesulfonate Saturation Mutagenesis in *Arabidopsis* to Determine Frequency of Herbicide Resistance; Plant Physiology, vol. 131, No. 1, pp. 139-146; (Jan. 2003).
Kanagasabapathi Sathasivan, George W.Haughn1 and Norimoto Murai; Nucleotide sequence of a mutant acetolactate synthase gene from an imidazolinone-resistant *Arabidopsis thaliana* var. Columbia; 2188 Nucleic Acids Research, vol. 18, No. 8; Oxford University Press; 1990.

* cited by examiner

*Primary Examiner* — Cathy Kingdon Worley
*Assistant Examiner* — Mykola Kovalenko
(74) *Attorney, Agent, or Firm* — Larson & Anderson, LLC

(57) ABSTRACT

The application discloses non-naturally occurring barley plants with increased resistance to herbicides, particularly imidazolinone herbicides. The imidazolinone resistance is conferred by mutant acetohydroxy acid synthase (AHAS), more particularly by AHAS with a SER653 mutation. Also disclosed are the barley seeds per se, an isolated nucleic acid incorporating the nucleic acid sequence conferring imidazolinone resistance, a method of inhibiting weed growth in the vicinity of a barley plant, an a method of growing a barley crop. Seeds have been deposited at NCIMB.

13 Claims, 9 Drawing Sheets

Figure 1

Sequence alignment of the imidazolinone resistant mutant lines (VBHT 0805, VBHT 0806, VBHT 0802 and VBHT 0810) and wild type comparators (AF059600, Buloke and Hindmarsh) for the AHAS gene localised around base 1742 (indicated by a box)

```
AF059600   ATCATTGTCCCGCATCAGGAGCACGTGCTGCCTATGATCCCAAGCGGTGGTGCTTTCAAGGACATGATCATG
Buloke     ATCATTGTCCCGCATCAGGAGCACGTGCTGCCTATGATCCCAAGCGGTGGTGCTTTCAAGGACATGATCATG
Hindmarsh  ATCATTGTCCCGCATCAGGAGCACGTGCTGCCTATGATCCCAAGCGGTGGTGCTTTCAAGGACATGATCATG
VBHT 0805  ATCATTGTCCCGCATCAGGAGCACGTGCTGCCTATGATCCCAAACGGTGGTGCTTTCAAGGACATGATCATG
VBHT 0806  ATCATTGTCCCGCATCAGGAGCACGTGCTGCCTATGATCCCAAACGGTGGTGCTTTCAAGGACATGATCATG
VBHT 0802  ATCATTGTCCCGCATCAGGAGCACGTGCTGCCTATGATCCCAAGCGGTGGTGCTTTCAAGGACATGATCATG
```

Figure 2

Amino acid sequence alignment of the AHAS gene for six plant species localised around mutant DNA nucleotide base 1742 identified in lines EMS05*06HI005 and EMS05*06HI006 (H.vulgare_AHAS_mutant) and the resulting alteration of a Serine (S) to an Asparagine (N)

```
N.tabacum_AHAS/1-24         H V L P M I P S G G A F K D V I T E G D G R S S
B.napus_AHAS1/1-24          H V L P M I P S G G T F K D V I T E G D G R T K
B.napus_AHAS2/1-24          H V L P M I P S G G T F K D V I T E G D G R T K
H.vulgare_AHAS/1-24         H V L P M I P S G G A F K D M I M E G D G R T S
H.vulgare_AHAS_mutant/1-24  H V L P M I P N G G A F K D M I M E G D G R T S
O.sativa_AHAS/1-24          H V L P M I P S G G A F K D M I L D G D G R T V
T.aestivum_AHAS/1-24        H V L P M I P S G G A F K D M I M E G D G R T S
Z.mays_AHAS/1-24            H V L P M I P S G G A F K D M I L D G D G R T V
```

Figure 3.

Alignment of resequenced AHAS gene for VBHT0802, VBHT0805, VBHT0806 and VBHT0810 compared to the wild type reference sequence (AHAS_H.vulgare_AF059600)

```
VBHT 0805           ------------------------------------------------
VBHT 0806           ----------CACCATCTACTGAATCGCTTGAGCAGGTCCTGCGCCTGGT
VBHT 0802           -------------CCATCTACTGAATCGCTTGAGCAGGTCCTGCGCCTGGT
AHAS_Hvulgare_AF059600  CTGCCCAAGCCACCATCTACTGAATCGCTTGAGCAGGTCCTGCGCCTGGT
VBHT 0810           --------------------CTGAATCGCTTGAGCAGGTCCTGCGCCTGGT
Buloke              ---------GCCACCATCTACTGAATCGCTTGAGCAGGTCCTGCGCCTGGT VBHT 0805           --------------------------GTATGTTGGTGGCGGCTGCGCTGCAT
VBHT 0806           TGGCGAGGCACGGCGCCCGATTCTGTATGTTGGTGGCGGCTGCGCTGCAT
VBHT 0802           TGGCGAGGCACGGCGCCCGATTCTGTATGTTGGTGGCGGCTGCGCTGCAT
AHAS_Hvulgare_AF059600  TGGCGAGGCACGGCGCCCGATTCTGTATGTTGGTGGCGGCTGCGCTGCAT
VBHT 0810           TGGCGAGGCACGGCGCCCGATTCTGTATGTTGGTGGCGGCTGCGCTGCAT
Buloke              TGGCGAGGCACGGCGCCCGATTCTGTATGTTGGTGGCGGCTGCGCTGCAT
                                              **************************

VBHT 0805           CTGGCGAGGAGTTGCGCCGCTTTGTTGAGCTCACTGGAATTCCAGTTACA
VBHT 0806           CTGGCGAGGAGTTGCGCCGCTTTGTTGAGCTCACTGGAATTCCAGTTACA
VBHT 0802           CTGGCGAGGAGTTGCGCCGCTTTGTTGAGCTCACTGGAATTCCAGTTACA
AHAS_Hvulgare_AF059600  CTGGCGAGGAGTTGCGCCGCTTTGTTGAGCTCACTGGAATTCCAGTTACA
VBHT 0810           CTGGCGAGGAGTTGCGCCGCTTTGTTGAGCTCACTGGAATTCCAGTTACA
Buloke              CTGGCGAGGAGTTGCGCCGCTTTGTTGAGCTCACTGGAATTCCAGTTACA
                    **************************************************

VBHT 0805           ACTACTCTGATGGGCCTTGGCAACTTCCCCAGTGACGACCCACTGTCACT
VBHT 0806           ACTACTCTGATGGGCCTTGGCAACTTCCCCAGTGACGACCCACTGTCACT
VBHT 0802           ACTACTCTGATGGGCCTTGGCAACTTCCCCAGTGACGACCCACTGTCACT
AHAS_Hvulgare_AF059600  ACTACTCTGATCGGCCTTGGCAACTTCCCCAGTGACGACCCACTGTCACT
VBHT 0810           ACTACTCTGATGGGCCTTGGCAACTTCCCCAGTGACGACCCACTGTCACT
Buloke              ACTACTCTGATGGGCCTTGGCAACTTCCCCAGTGACGACCCACTGTCACT
                    ***********  *************************************

VBHT 0805           GCGCATGCTTGGGATGCATGGTACCGTGTATGCAAATTATGCAGTAGATA
VBHT 0806           GCGCATGCTTGGGATGCATGGTACCGTGTATGCAAATTATGCAGTAGATA
VBHT 0802           GCGCATGCTTGGGATGCATGGTACCGTGTATGCAAATTATGCAGTAGATA
AHAS_Hvulgare_AF059600  GCGCATGCTTGGGATGCATGGTACCGTGTATGCAAATTATGCAGTAGATA
VBHT 0810           GCGCATGCTTGGGATGCATGGTACCGTGTATGCAAATTATGCAGTAGATA
Buloke              GCGCATGCTTGGGATGCATGGTACCGTGTATGCAAATTATGCAGTAGATA
                    **************************************************

VBHT 0805           AGGCTGACCTGTTGCTTGCATTTGGTGTGCGGTTTGATGATCGCGTGACT
VBHT 0806           AGGCTGACCTGTTGCTTGCATTTGGTGTGCGGTTTGATGATCGCGTGACT
VBHT 0802           AGGCTGACCTGTTGCTTGCATTTGGTGTGCGGTTTGATGATCGCGTGACT
AHAS_Hvulgare_AF059600  AGGCTGACCTGTTGCTTGCATTTGGTGTGCGGTTTGATGATCGCGTGACT
VBHT 0810           AGGCTGACCTGTTGCTTGCATTTGGTGTGCGGTTTGATGATCGCGTGACT
Buloke              AGGCTGACCTGTTGCTTGCATTTGGTGTGCGGTTTGATGATCGCGTGACT
                    **************************************************

VBHT 0805           GGGAAAATTGAGGCTTTTGCAAGCAGGTCCAAGATTGTGCACATTGACAT
VBHT 0806           GGGAAAATTGAGGCTTTTGCAAGCAGGTCCAAGATTGTGCACATTGACAT
VBHT 0802           GGGAAAATTGAGGCTTTTGCAAGCAGGTCCAAGATTGTGCACATTGACAT
AHAS_Hvulgare_AF059600  GGGAAAATTGAGGCTTTTGCAAGCAGGTCCAAGATTGTGCACATTGACAT
VBHT 0810           GGGAAAATTGAGGCTTTTGCAAGCAGGTCCAAGATTGTGCACATTGACAT
Buloke              GGGAAAATTGAGGCTTTTGCAAGCAGGTCCAAGATTGTGCACATTGACAT
                    **************************************************

VBHT 0805           TGATCCAGCTGAGATTGGCAACAACAAGCAGCCACATGTCTCCATTTGTG
VBHT 0806           TGATCCAGCTGAGATTGGCAAGAACAAGCAGCCACATGTCTCCATTTGTG
VBHT 0802           TGATCCAGCTGAGATTGGCAAGAACAARCAGCCACATGTCTCCATTTGTG
AHAS_Hvulgare_AF059600  TGATCCAGCTGAGATTGGCAAGAACAAGCAGCCACATGTCTCCATTTGTG
VBHT 0810           TGATCCAGCTGAGATTGGCAAGAACAAGCAGCCACATGTCTCCATTTGTG
Buloke              TGATCCAGCTGAGATTGGCAAGAACAAGCAGCCACATGTCTCCATTTGTG
                    ********************* * ************************

VBHT 0805           CAGATGTTAAGCTTGCTTTACAGGGGTTGAATGGTCTATTAAGTGGCAGC
VBHT 0806           CAGATGTTAAGCTTGCTTTACAGGGGTTGAATGGTCTATTAAGTGGCAGC
VBHT 0802           CAGATGTTAAGCTTGCTTTACAGGGGTTGAATGGTCTATTAAGTGGCAGC
AHAS_Hvulgare_AF059600  CAGATGTTAAGCTTGCTTTACAGGGGTTGAATGGTCTATTAAGTGGCAGC
VBHT 0810           CAGATGTTAAGCTTGCTTTACAGGGGTTCAATGGTCTATTAAGTGGCAGC
Buloke              CAGATGTTAAGCTTGCTTTACAGGGGTTGAATGGTCTATTAAGTGGCAGC
                    **************************************************
```

Figure 3, cont'd

```
VBHT 0805              AAAGCACAACAGGGTCTAGATTTTGGTCCATGGCACAAGGAGTTGGATCA
VBHT 0806              AAAGCACAACAGGGTCTAGATTTTGGTCCATGGCACAAGGAGTTGGATCA
VBHT 0802              AAAGCACAACAGGGTCTAGATTTTGGTCCATGGCACAAGGAGTTGGATCA
AHAS_Hvulgare_AF059600 AAAGCACAACAGGGTCTAGATTTTGGTCCATGGCACAAGGAGTTGGATCA
VBHT 0810              AAAGCACAACAGGGTCTAGATTTTGGTCCATGGCACAAGGAGTTGGATCA
Buloke                 AAAGCACAACAGGGTCTAGATTTTGGTCCATGGCACAAGGAGTTGGATCA
                       **************************************************

VBHT 0805              GCAGAAGAGGGAGTTTCCTCTAGGATACAAGACTTTTGGTGAGGCAATCC
VBHT 0806              GCAGAAGAGGGAGTTTCCTCTAGGATACAAGACTTTTGGTGAGGCAATCC
VBHT 0802              GCAGAAGAGGGAGTTTCCTCTAGGATACAAGACTTTTGGTGAGGCAATCC
AHAS_Hvulgare_AF059600 GCAGAAGAGGGAGTTTCCTCTAGGATACAAGACTTTTGGTGAGGCAATCC
VBHT 0810              GCAGAAGAGGGAGTTTCCTCTAGGATACAAGACTTTTGGTGAGGCAATCC
Buloke                 GCAGAAGAGGGAGTTTCCTCTAGGATACAAGACTTTTGGTGAGGCAATCC
                       **************************************************

VBHT 0805              CACCGCAGTATGCTATCCAGGTACTGGATGAGCTGACAAAAGGGGAGGCG
VBHT 0806              CACCGCAGTATGCTATCCAGGTACTGGATGAGCTGACAAAAGGGGAGGCG
VBHT 0802              CACCGCAGTATGCTATCCAGGTACTGGATGAGCTGACAAAAGGGGAGGCG
AHAS_Hvulgare_AF059600 CACCGCAGTATGCTATCCAGGTACTGGATGAGCTGACAAAAGGGGAGGCG
VBHT 0810              CACCGCAGTATGCTATCCAGGTACTGGATGAGCTGACAAAAGGGGAGGCG
Buloke                 CACCGCAGTATGCTATCCAGGTACTGGATGAGCTGACAAAAGGGGAGGCG
                       **************************************************

VBHT 0805              ATTATTGCCACAGGTGTTGGGCAGCATCAGATGTGGGCGGCTCAGTATTA
VBHT 0806              ATTATTGCCACAGGTGTTGGGCAGCATCAGATGTGGGCGGCTCAGTATTA
VBHT 0802              ATTATTGCCACAGGTGTTGGGCAGCATCAGATGTGGGCGGCTCAGTATTA
AHAS_Hvulgare_AF059600 ATTATTGCCACAGGTGTTGGGCAGCATCAGATGTGGGCGGCTCAGTATTA
VBHT 0810              ATTATTGCCACAGGTGTTGGGCAGCATCAGATGTGGGCGGCTCAGTATTA
Buloke                 ATTATTGCCACAGGTGTTGGGCAGCATCAGATGTGGGCGGCTCAGTATTA
                       **************************************************

VBHT 0805              CACTTACAAGCGGCCACGTCAGTGGCTGTCTTCGTCTGGTTTGGGGGCAA
VBHT 0806              CACTTACAAGCGGCCACGTCAGTGGCTGTCTTCGTCTGGTTTGGGGGCAA
VBHT 0802              CACTTACAAGCGGCCACGTCAGTGGCTGTCTTCGTCTGGTTTGGGGGCAA
AHAS_Hvulgare_AF059600 CACTTACAAGCGGCCACGTCAGTGGCTGTCTTCGTCTGGTTTGGGGGCAA
VBHT 0810              CACTTACAAGCGGCCACGTCAGTGGCTGTCTTCGTCTGGTTTGGGGGCAA
Buloke                 CACTTACAAGCGGCCACGTCAGTGGCTGTCTTCGTCTGGTTTGGGGGCAA
                       **************************************************

VBHT 0805              TGGGATTTGGGTTGCCAGCTGCAGCTGGCGCTTCTGTGGCCAACCCCAGGT
VBHT 0806              TGGGATTTGGGTTGCCAGCTGCAGCTGGCGCTTCTGTGGCCAACCCCAGGT
VBHT 0802              TGGGATTTGGGTTGCCAGCTGCAGCTGGCGCTTCTGTGGCCAACCCCAGGT
AHAS_Hvulgare_AF059600 TGGGATTTGGGTTGCCAGCTGCAGCTGGCGCTTCTGTGGCCAACCCCAGGT
VBHT 0810              TGGGATTTGGGTTGCCAGCTGCAGCTGGCGCTTCTGTGGCCAACCCCAGGT
Buloke                 TGGGATTTGGGTTGCCAGCTGCAGCTGGCGCTTCTGTGGCCAACCCCAGGT
                       **************************************************

VBHT 0805              GTCACAGTTGTTGACATTGATGGGGATGGTAGTTTCCTCATGAACATTCA
VBHT 0806              GTCACAGTTGTTGACATTGATGGGGATGGTAGTTTCCTCATGAACATTCA
VBHT 0802              GTCACAGTTGTTGACATTGATGGGGATGGTAGTTTCCTCATGAACATTCA
AHAS_Hvulgare_AF059600 GTCACAGTTGTTGACATTGATGGGGATGGTAGTTTCCTCATGAACATTCA
VBHT 0810              GTCACAGTTGTTGACATTGATGGGGATGGTAGTTTCCTCATGAACATTCA
Buloke                 GTCACAGTTGTTGACATTGATGGGGATGGTAGTTTCCTCATGAACATTCA
                       **************************************************

VBHT 0805              GGAGTTGGCCGTTGATCCGTATTGAGAACCTCCCAGTGAAGGTGATGATAT
VBHT 0806              GGAGTTGGCGTTGATCCGTATTGAGAACCTCCCAGTGAAGGTGATGATAT
VBHT 0802              GGAGTTGGCGTTGATCCGTATTGAGAACCTCCCAGTGAAGGTGATGATAT
AHAS_Hvulgare_AF059600 GGAGTTGGCGTTGATCCGTATTGAGAACCTCCCAGTGAAGGTGATGATAT
VBHT 0810              GGAGTTGGCATTGATCCGTATTGAGAACCTCCCAGTGAAGGTGATGATAT
Buloke                 GGAGTTGGCGTTGATCCGTATTGAGAACCTCCCAGTGAAGGTGATGATAT
                       ******** *****************************************

VBHT 0805              TGAACAACCAGCACCTGGGAATGGTGGTGCAGTGGGAGGATAGGTTTTAC
VBHT 0806              TGAACAACCAGCACCTGGGAATGGTGGTGCAGTGGGAGGATAGGTTTTAC
VBHT 0802              TGAACAACCAGCACCTGGGAATGGTGGTGCAGTGGGAGGATAGGTTTTAC
AHAS_Hvulgare_AF059600 TGAACAACCAGCACCTGGGAATGGTGGTGCAGTGGGAGGATAGGTTTTAC
VBHT 0810              TGA-----------------------------------------------
Buloke                 TGAACAACCAGCACCTGGGAATGGTGGTGCAGTGGGAGGATAGGTTTTAC
                       ***
```

Figure 3, cont'd

```
VBHT 0805              AAGGCCAACCGGGCGCACACATACCTTGGCAACCCAGAAAATGAGAGTGA
VBHT 0806              AAGGCCAACCGGGCGCACACATACCTTGGCAACCCAGAAAATGAGAGTGA
VBHT 0802              AAGGCCAACCGGGCGCACACATACCTTGGCAACCCAGAAAATGAGAGTGA
AHAS_Hvulgare_AF059600 AAGGCCAACCGGGCGCACACATACCTTGGCAACCCAGAAAATGAGAGTGA
VBHT 0810              --------------------------------------------------
Buloke                 AAGGCCAACCGGGCGCACACATACCTTGGCAACCCAGAAAATGAGAGTGA VBHT 0805              GATATATCCAGATTTTGTGACGATTGCTAAAGGATTCAATGTTCCGGCAG
VBHT 0806              GATATATCCAGATTTTGTGACGATTGCTAAAGGATTCAATGTTCCGGCAG
VBHT 0802              GATATATCCAGATTTTGTGACGATTGCTAAAGGATTCAATGTTCCGGCAG
AHAS_Hvulgare_AF059600 GATATATCCAGATTTTGTGACGATTGCTAAAGGATTCAATGTTCCGGCAG
VBHT 0810              --------------------------------------------------
Buloke                 GATATATCCAGATTTTGTGACGATTGCTAAAGGATTCAATGTTCCGGCAG VBHT 0805              TTCGTGTGACAAAGAAGAGTGAAGTCAGTGCAGCTATCAAGAAGATGCTT
VBHT 0806              TTCGTGTGACAAAGAAGAGTGAAGTCAGTGCAGCTATCAAGAAGATGCTT
VBHT 0802              TTCGTGTGACAAAGAAGAGTGAAGTCAGTGCAGCTATCAAGAAGATGCTT
AHAS_Hvulgare_AF059600 TTCGTGTGACAAAGAAGAGTGAAGTCAGTGCAGCTATCAAGAAGATGCTT
VBHT 0810              --------------------------------------------------
Buloke                 TTCGTGTGACAAAGAAGAGTGAAGTCAGTGCAGCTATCAAGAAGATGCTT VBHT 0805              GAGACCCCAGGGCCGTACCTGCTGGATATCATTGTCCCGCATCAGGAGCA
VBHT 0806              GAGACCCCAGGGCCGTACCTGCTGGATATCATTGTCCCGCATCAGGAGCA
VBHT 0802              GAGACCCCAGGGCCGTACCTGCTGGATATCATTGTCCCGCATCAGGAGCA
AHAS_Hvulgare_AF059600 GAGACCCCAGGGCCGTACCTGCTGGATATCATTGTCCCGCATCAGGAGCA
VBHT 0810              --------------------------------------------------
Buloke                 GAGACCCCAGGGCCGTACCTGCTGGATATCATTGTCCCGCATCAGGAGCA VBHT 0805              CGTGCTGCCTATGATCCCAAACGGTGGTGCTTTCAAGGACATGATCATG-
VBHT 0806              CGTGCTGCCTATGATCCCAAACGGTGGTGCTTTCAAGGACATGATCATGG
VBHT 0802              CGTGCTGCCTATGATCCCAAGCGGTGGTGCTTTCAAGGACATGATCATGG
AHAS_Hvulgare_AF059600 CGTGCTGCCTATGATCCCAAGCGGTGGTGCTTTCAAGGACATGATCATGG
VBHT 0810              --------------------------------------------------
Buloke                 CGTGCTGCCTATGATCCCAAGCGGTGGTGCTTTCAAGGACATGATCATGG VBHT 0805              --------------------------
VBHT 0806              AGG-----------------------
VBHT 0802              AG------------------------
AHAS_Hvulgare_AF059600 AGGGTGATGGCAGGACCTCGTACTGA
VBHT 0810              --------------------------
Buloke                 AGG-----------------------
```

Figure 4

Table 3: 2007 Horsham

| Name | Synonym | Grain yield (t/ha) | |
|---|---|---|---|
| | | Control - No Intervix® applied | Intervix® applied (0.75L/ha) |
| Buloke | | 2.13 | 0# |
| Hindmarsh | | 2.14 | 0# |
| VBHT0802 | BULOKE-EMS05*06HI002 | 2.64 | 2.61 |
| VBHT0805 | BULOKE-EMS05*06HI005 | 2.51 | 2.72 |
| VBHT0806 | BULOKE-EMS05*06HI006 | 2.12 | 2.36 |
| VBHT0810 | BULOKE-EMS05*06HI010 | 2.34 | 2.41 |
| SE | | 0.20 | |
| LSD | | 0.35 | |
| CV (%) | | 9.80 | | significant yield reduction compared to control (no intervix applied)

Table 4: 2008 Horsham

| Name | Synonym | Grain yield (t/ha) | | | |
|---|---|---|---|---|---|
| | | Control - No Intervix® applied | Intervix® applied (0.375L/ha) | Intervix® applied (0.75L/ha) | Intervix® applied (1.5L/ha) |
| BULOKE | | 1.34 | 0.022# | 0.023# | 0.022# |
| HINDMARSH | | 1.50 | 0.017# | 0.012# | 0.034# |
| VBHT0802 | BULOKE-EMS05*06HI002 | 1.45 | 1.54 | 1.33 | 1.42 |
| VBHT0805 | BULOKE-EMS05*06HI005 | 1.43 | 1.66 | 1.36 | 1.55 |
| VBHT0806 | BULOKE-EMS05*06HI006 | 1.31 | 1.33 | 1.28 | 1.35 |
| VBHT0810 | BULOKE-EMS05*06HI010 | 1.36 | 1.45 | 1.33 | 1.42 |
| SE | | 0.13 | | | |
| LSD | | 0.22 | | | |
| CV (%) | | 15.32 | | | | significant yield reduction compared to control (no intervix applied)

Table 5: 2008 Marinna

| Name | Synonym | Grain yield (t/ha) | | | |
|---|---|---|---|---|---|
| | | Control - No Intervix® applied | Intervix® applied (0.375L/ha) | Intervix® applied (0.75L/ha) | Intervix® applied (1.25L/ha) |
| BULOKE | | 0.84 | 0.00# | 0.00# | 0.00# |
| HINDMARSH | | 1.12 | 0.00# | 0.00# | 0.00# |
| VBHT0802 | BULOKE-EMS05*06HI002 | 1.00 | 1.12 | 1.18 | 1.08 |
| VBHT0805 | BULOKE-EMS05*06HI005 | 1.07 | 1.26 | 1.21 | 1.25 |
| VBHT0806 | BULOKE-EMS05*06HI006 | 1.02 | 0.96 | 1.00 | 1.00 |
| VBHT0810 | BULOKE-EMS05*06HI010 | 0.99 | 1.09 | 1.23 | 1.00 |
| SE | | 0.20 | | | |
| LSD | | 0.13 | | | |
| CV (%) | | 34.20 | | | | significant yield reduction compared to control (no intervix applied)

Table 6: Yield (t/ha) of imidazolinone resistant mutant lines compared with Buloke at 9 sites in Australia.

| name | Paskeville | Callington | Forbes | Temora | Junee Reefs | Dimboola | Elmore | Mt Mercer | Northam early | Northam late | Mean yield (t/ha) | Mean yield (% Buloke) |
|---|---|---|---|---|---|---|---|---|---|---|---|---|
| BULOKE | 4.40 | 3.88 | 1.48 | 1.61 | 3.79 | 3.72 | 4.92 | 2.73 | 2.89 | 1.91 | 3.13 | 100 |
| VBHT0802 | 4.52 | 3.99 | 1.35 | 1.55 | 3.84 | 4.08 | 4.89 | 2.86 | 3.10 | 2.28 | 3.25 | 104 |
| VBHT0805 | 4.71 | 3.78 | 1.57 | 1.55 | 3.84 | 3.72 | 4.89 | 3.25 | 3.19 | 2.03 | 3.25 | 104 |
| VBHT0806 | 4.53 | 3.78 | 1.57 | 1.60 | 3.49 | 3.60 | 4.70 | 2.27 | 2.55 | 2.04 | 3.01 | 96 |
| VBHT0810 | 4.50 | 3.93 | 1.39 | 1.51 | 3.87 | 3.88 | 4.92 | 3.20 | 3.11 | 2.04 | 3.23 | 103 |
| Site mean | 4.48 | 3.92 | 1.67 | 1.61 | 3.86 | 3.84 | 4.84 | 2.82 | 2.97 | 1.90 | | |
| CV | 3.3 | 3.8 | 12.0 | 10.0 | 6.0 | 7.2 | 3.4 | 10.2 | 5.2 | 9.6 | | |
| LSD | 0.30 | 0.22 | 0.55 | 0.32 | 0.46 | 0.55 | 0.32 | 0.32 | 0.31 | 0.30 | | |

Figure 5

TABLE 7 : Morphological and DNA comparison of imidazolinone resistant mutant barley lines with parent cultivar Buloke

| Name | Synonym | Morphological characteristics that differ from the wild type Buloke | Analysis of 1424 SNP markers in comparison to the Buloke reference sample (VB0105*12) | Mutation in the AHAS gene known to confer resistance to imidazolinone |
|---|---|---|---|---|
| VBHT0802 | BULOKE-EMS05*06HI002 | Small grain size and lower HWE | Differed from Buloke at 5 SNP loci. | Unknown |
| VBHT0803 | BULOKE-EMS05*06HI003-06GI003 | Purple awns Shorter than Buloke but not dwarf Larger grain size but lower HWE | Differed from Buloke at 223 SNP loci. | NOT an alteration of coordinate 1742 changing a G to an A, altering the amino acid from a serine to an asparagine. |
| VBHT0805 | BULOKE-EMS05*06HI005 | Similar to Buloke | Differed from Buloke at 41 SNP loci Identical haplotype to VBHT0807 and VBHT0810 | Unknown |
| VBHT0806 | BULOKE-EMS05*06HI006 | Similar to Buloke | Differed from Buloke at 138 SNP loci. | Alteration of coordinate 1742 changing a G to an A, altering the amino acid from a serine to an asparagine. |
| VBHT0807 | BULOKE-EMS05*06HI007-06GI001 | Similar to Buloke | Differed from Buloke at 41 SNP loci Identical haplotype to VBHT0805 and VBHT0810 | Alteration of coordinate 1742 changing a G to an A, altering the amino acid from a serine to an asparagine. |
| VBHT0809 | BULOKE-EMS05*06HI009-06G082 | Purple awns Prostrate growth habit Shorter than Buloke - dwarf | Differed from Buloke at 237 SNP loci. | Unknown |
| VBHT0810 | BULOKE-EMS05*06HI010 | Similar to Buloke | Differed from Buloke at 41 SNP loci Identical haplotype to VBHT0805 and VBHT0807 | Unknown |

Figure 6

TABLE 8: MALTING QUALITY FOR VBHT0805 COMPARED TO BULOKE

| Name | Hectolitre weight (kg/hl) | Plump grain – grain retained on a sieve (%) | | Screenings – grain passing through a 2.2mm sieve (%) | Weight of 1000 kernels (grams) | Kernal colour CIE L* a* b* | | | Protein – dry basis (%) | Hot water extract – dry basis (%) | Hot water extract /protein | Viscosity (cP) |
|---|---|---|---|---|---|---|---|---|---|---|---|---|
| | | >2.8 mm | >2.5 mm | | | L* | a* | b* | | | | |
| Buloke | 72.2 | 14.8 | 72.2 | 0.4 | 46.1 | 63.3 | 4.8 | 22.3 | 10.9 | 81.4 | 7.5 | 1.6 |
| VBHT0805 | 72.3 | 17.8 | 79.8 | 0.1 | 45.1 | 63.3 | 4.8 | 22.6 | 10.9 | 81.6 | 7.5 | 1.6 |

Figure 7

SEQUENCE LISTING

```
<160> NUMBER OF SEQ ID NOS: 4

<210> SEQ ID NO 1
<211> LENGTH: 1075
<212> TYPE: DNA
<213> ORGANISM: Hordeum vulgare

<400> SEQUENCE: 1
gtatgttggt ggcggctgcg ctgcatctgg cgaggagttg cgccgctttg ttgagctcac      60
tggaattcca gttacaacta ctctgatggg ccttggcaac ttccccagtg acgacccact     120
gtcactgcgc atgcttggga tgcatggtac cgtgtatgca aattatgcag tagataaggc     180
tgacctgttg cttgcatttg gtgtgcggtt tgatgatcgc gtgactggga aaattgaggc     240
ttttgcaagc aggtccaaga ttgtgcacat tgacattgat ccagctgaga ttggcaagaa     300
caagcagcca catgtctcca tttgtgcaga tgttaagctt gctttacagg ggttgaatgg     360
tctattaagt ggcagcaaag cacaacaggg tctagatttt ggtccatggc acaaggagtt     420
ggatcagcag aagagggagt ttcctctagg atacaagact tttggtgagg caatcccacc     480
gcagtatgct atccaggtac tggatgagct gacaaaaggg gaggcgatta ttgccacagg     540
tgttgggcag catcagatgt gggcggctca gtattacact tacaagcggc cacgtcagtg     600
gctgtcttcg tctggtttgg gggcaatggg atttggttta ccagctgcag ctggcgcttc     660
tgtggccaac ccaggtgtca cagttgttga cattgatggg gatggtagtt tcctcatgaa     720
cattcaggag ttggcgttga tccgtattga gaacctccca gtgaaggtga tgatattgaa     780
caaccagcac ctgggaatgg tggtgcagtg ggaggatagg ttttacaagg ccaaccgggc     840
gcacacatac cttggcaacc cagaaaatga gagtgagata tatccagatt ttgtgacgat     900
tgctaaagga ttcaatgttc cggcagttcg tgtgacaaag aagagtgaag tcagtgcagc     960
tatcaagaag atgcttgaga ccccagggcc gtacctgctg gatatcattg tcccgcatca    1020
ggagcacgtg ctgcctatga tcccaaacgg tggtgctttc aaggacatga tcatg         1075
```

<210> SEQ ID NO 2
<211> LENGTH: 1143
<212> TYPE: DNA
<213> ORGANISM: Hordeum vulgare

<400> SEQUENCE: 2

| | | | | | |
|---|---|---|---|---|---|
| caccatctac | tgaatcgctt | gagcaggtcc | tgcgcctggt | tggcgaggca | cggcgcccga | 60 |
| ttctgtatgt | tggtggcggc | tgcgctgcat | ctggcgagga | gttgcgccgc | tttgttgagc | 120 |
| tcactggaat | tccagttaca | actactctga | tgggccttgg | caacttcccc | agtgacgacc | 180 |
| cactgtcact | gcgcatgctt | gggatgcatg | gtaccgtgta | tgcaaattat | gcagtagata | 240 |
| aggctgacct | gttgcttgca | tttggtgtgc | ggtttgatga | tcgcgtgact | gggaaaattg | 300 |
| aggcttttgc | aagcaggtcc | aagattgtgc | acattgacat | tgatccagct | gagattggca | 360 |
| agaacaagca | gccacatgtc | tccatttgtg | cagatgttaa | gcttgcttta | caggggttga | 420 |
| atggtctatt | aagtggcagc | aaagcacaac | agggtctaga | ttttggtcca | tggcacaagg | 480 |
| agttggatca | gcagaagagg | gagtttcctc | taggatacaa | gacttttggt | gaggcaatcc | 540 |
| caccgcagta | tgctatccag | gtactggatg | agctgacaaa | aggggaggcg | attattgcca | 600 |
| caggtgttgg | gcagcatcag | atgtgggcgg | ctcagtatta | cacttacaag | cggccacgtc | 660 |
| agtggctgtc | ttcgtctggt | ttgggggcaa | tgggatttgg | gttgccagct | gcagctggcg | 720 |
| cttctgtggc | caacccaggt | gtcacagttg | ttgacattga | tggggatggt | agttccctca | 780 |
| tgaacattca | ggagttggcg | ttgatccgta | ttgagaacct | cccagtgaag | gtgatgatat | 840 |
| tgaacaacca | gcacctggga | atggtggtgc | agtgggagga | taggttttac | aaggccaacc | 900 |
| gggcgcacac | ataccttggc | aacccagaaa | atgagagtga | gatatatcca | gattttgtga | 960 |
| cgattgctaa | aggattcaat | gttccggcag | ttcgtgtgac | aaagaagagt | gaagtcagtg | 1020 |
| cagctatcaa | gaagatgctt | gagaccccag | ggccgtacct | gctggatatc | attgtcccgc | 1080 |
| atcaggagca | cgtgctgcct | atgatcccaa | acggtggtgc | tttcaaggac | atgatcatgg | 1140 |
| agg | | | | | | 1143 |

<210> SEQ ID NO 3
<211> LENGTH: 395
<212> TYPE: DNA
<213> ORGANISM: Hordeum vulgare

<400> SEQUENCE: 3

| | | | | | |
|---|---|---|---|---|---|
| atggggatgg | tagtttcctc | atgaacattc | aggagttggc | gttgatccgt | attgagaacc | 60 |
| tcccagtgaa | ggtgatgata | ttgaacaacc | agcacctggg | aatggtggtg | cagtgggagg | 120 |
| ataggtttta | caaggccaac | cgggcgcaca | cataccttgg | caacccagaa | atgagagtg | 180 |
| agatatatcc | agattttgtg | acgattgcta | aaggattcaa | tgttccggca | gttcgtgtga | 240 |
| caaagaagag | tgaagtcagt | gcagctatca | agaagatgct | tgagacccca | gggccgtacc | 300 |
| tgctggatat | cattgtcccg | catcaggagc | acgtgctgcc | tatgatccca | aacggtggtg | 360 |
| ctttcaagga | catgatcatg | gagggtgatg | gcagg | | | 395 |

<210> SEQ ID NO 4
<211> LENGTH: 24
<212> TYPE: PRT
<213> ORGANISM: Hordeum vulgare

<400> SEQUENCE: 4

His Val Leu Pro Met Ile Pro Asn Gly Gly Ala Phe Lys Asp Met Ile
1               5                   10                  15

```
Met Glu Gly Asp Gly Arg Thr Ser
            20
```

HERBICIDE RESISTANT BARLEY EXPRESSING MUTANT ACETOHYDROXY ACID SYNTHASE

FIELD OF THE INVENTION

The present invention relates to grain plants having herbicide resistance or tolerance. More specifically the present invention relates to herbicide resistant barley plants.

BACKGROUND OF THE INVENTION

Food production, particularly grain production is of increasing importance worldwide due to growing populations and other pressures such as reduction in arable land, climate change and the increasing use of crops for biofuel production.

Herbicides play an important role in modern agriculture by maximizing grain production, pasture production, quality and profitability. Herbicides allow undesirable plants to be killed or suppressed and thereby reduce competition with desirable plants such as crop plants for nutrients, water and the like.

Imidazolinone and sulphonylurea herbicides inhibit the growth and development of susceptible plants, including a wide range of weeds, by inhibiting the plant enzyme Acetohydroxy acid synthase (AHAS), also known as acetolactate synthase (ALS). AHAS synthesizes branch chain amino acids, a key function in plants. Importantly, imidazolinone and sulphonylurea herbicides also have relatively low toxicity to animals, including humans.

Imidazolinones include the following compounds imazethapyr, imazaquin, imazapyr, imazapic, imazamox and the like.

Commercially available imidazolinone herbicides include ON DUTY® (imazapic+imazapyr) INTERVIX® (imazamox+imazapyr) SPINNAKER® (imazethapyr), RAPTOR® (imazamox) and FLAME® (imazapic).

Although naturally occurring resistance to herbicides has been described in some crops many important food crops are susceptible to herbicides including imidazolinone.

Barley (*Hordeum vulgare*) is an important grain crop internationally because it is used in malt production, brewing and for human and animal feed. It has the advantage of being more salt tolerant than wheat and can be grown successfully on poorer quality land and/or in drier environments.

Weed control is a major issue in barley production. Good chemical weed control is desirable to maximize production of the crop and limit the need for mechanical cultivation and resultant damage to soil structure and erosion. In particular it would be desirable to utilize a greater range of low toxicity herbicides to control the full spectrum of a variety of weeds in a barley cropping system. For example, as most barley is resistant to sulphonylureas, this herbicide can be applied post emergence to growing barley crops, however, imidazolinones cannot be applied post emergence because barley is susceptible to this class of herbicides. Further, the crop cannot even be sown into soil containing imidazolinones because of its susceptibility to this herbicide.

The above references to and descriptions of prior proposals or products are not intended to be, and are not to be construed as, statements or admissions of common general knowledge in the art.

SUMMARY OF THE INVENTION

The invention provides a non-naturally occurring barley plant which has increased resistance to herbicides compared with the wild type barley.

The invention also provides a seed of the non-naturally occurring barley plant.

Further the invention provides a method of inhibiting weed growth in the vicinity of a barley plant comprising growing a barley plant with increased resistance to a herbicide compared to a wild type barley plant and applying under suitable conditions imidazolinone to said barley plant with increased resistance and its vicinity sufficient to inhibit weed growth.

The invention also relates to a method of growing a barley crop comprising sowing the seeds of the invention and cultivating the seeds and resultant plants under suitable conditions to produce a crop.

BRIEF DESCRIPTION OF THE FIGURES

FIG. 1 shows a sequence alignment for the AHAS gene localised around base 1742 (indicated by a box) of the following imidazolinone resistant mutant lines:
VBHT 0805 (SEQ ID NO: 8)
VBHT 0806 (SEQ ID NO: 9)
VBHT 0802 (SEQ ID NO: 10)
and the following wild type comparators:
AF059600 (SEQ ID NO: 5)
Buloke (SEQ ID NO: 6)
Hindmarsh (SEQ ID NO: 7).

FIG. 2 shows amino acid sequence alignment of the AHAS gene for six plant species localised around mutant DNA nucleotide base 1742 identified in lines EMS05*06HI005 and EMS05*06HI006 (*H.vulgare*_AHAS_mutant) and the resulting alteration of a Serine (S) to an Asparagine (N):
Nicotiana tabacum AHAS/1-24 (SEQ ID NO: 11)
Brassica napus AHAS1/1-24 (SEQ ID NO: 12)
Brassica napus AHAS2/1-24 (SEQ ID NO: 13)
*Hordeum vulgare* AHAS/1-24 (SEQ ID NO: 14)
*Hordeum vulgare* AHAS mutant/1-24 (SEQ ID NO: 15)
Oryza sativa AHAS/1-24 (SEQ ID NO: 16)
Triticum aestivum AHAS/1-24 (SEQ ID NO: 17)
Zea mays AHAS/1-24 (SEQ ID NO: 18).

FIG. 3 shows alignment of resequenced AHAS gene for VBHT 0805, VBHT 0806, VBHT 0802 and VBHT 0810 compared to the wild type reference sequences (AHAS_*H.vulgare*_AF059600 and Buloke):
VBHT 0805 (SEQ ID NO: 1)
VBHT 0806 (SEQ ID NO: 2)
VBHT 0802 (SEQ ID NO: 19)
AHAS *H. vulgare* AF059600 (SEQ ID NO: 20)
VBHT 0810 (SEQ ID NO: 21)
Buloke (SEQ ID NO: 22).

FIG. 4 shows the imidazolinone resistance of the mutated lines VBHT0802, VBHT0805, VBHT0806 and VBHT0810 compared to the wild type lines Buloke and Hindmarsh in experiments at Horsham, Victoria, Australia in 2007 (Table 3), and 2008 (Table 4) and at Marinna, NSW, Australia in 2008 (Table 5). The experiments are described in Example 5.

FIG. 5 shows in Table 6 yield (t/ha) of imidazolinone resistant mutant lines compared with Buloke at 9 sites in Australia. The experiments are described in Example 6.

FIG. 6 shows in Table 7 morphological and DNA comparison of imidazolinone resistant mutant barley lines with parent cultivar Buloke. The experiments are described in Example 7.

FIG. 7 shows in Table 8 malting quality for VBHT0805 compared to Buloke. The experiments are described in Example 10.

DETAILED DESCRIPTION OF THE INVENTION

The invention provides a non-naturally occurring barley plant which has increased resistance to herbicides compared to wild type barley, particularly resistance to imidazolinone herbicides. Progeny of the barley plants and descendants having the increased herbicide resistance trait or characteristic are also included in the invention. The invention also includes hybrids of the barley plants of the invention.

The term "non-naturally occurring" refers to a plant which does not occur in nature and is the result of human intervention. Preferably the plants are produced by mutagenesis, more preferably chemically induced mutagenesis.

The term "barley plant" refers to the species *Hordeum vulgare* in its total genetic variation and its many varieties such as Buloke and Hindmarsh, and to related species within the *Hordeum* genus.

The terms "increased resistance to herbicides" and "herbicide resistant barley" mean that the plant is not as adversely affected by the herbicide as its naturally occurring counterpart or wild type. The term includes tolerance to herbicides.

The invention further provides a seed of the non-naturally occurring barley plant which has increased resistance to herbicides, particularly imidazolinone herbicides.

While not wishing to be bound by theory, it appears that the increased herbicide resistance developed by the present inventors results from changes to the physiology and/or biochemistry of the plant and thus interferes with the normal action of the herbicide. This may involve altered absorption and/or translocation of the herbicide or altered ability of metabolic enzymes to bind the herbicide. Thus the invention extends to the altered elements in the plant that confer herbicide resistance including altered gene(s) and/or protein(s) including enzymes, which genes and proteins are altered compared to their counterparts in herbicide sensitive barley plants. Preferably said altered genes and/or proteins are in isolated or substantially purified form.

The plants and seeds of the invention include plants and seeds that are mutations, recombinant variants and genetically engineered derivatives or derivatives derived by other means such as conventional breeding, which retain the altered elements described above. The invention also extends to plant parts other than seeds of the herbicide resistant barley, including plant cells, plant tissues and plant organs whether produced by plant tissue culture or otherwise.

The invention also provides a method of inhibiting weed growth in the vicinity of a barley plant comprising growing a barley plant with increased resistance to a herbicide compared to a wild type barley plant and applying under suitable conditions imidazolinone to said barley plant and vicinity sufficient to inhibit weed growth.

The invention also relates to a method of inhibiting weed growth in a barley crop said method comprising growing a herbicide resistant barley crop and applying a imidazolinone herbicide to said crop under suitable conditions to inhibit weed growth.

The imidazolinone may be used as a combination of imazamox and imazapyr at a rate of 12.375 g per hectare and 5.625 g per hectare respectively; 24.75 and 11.25 g per hectare respectively; 41.25 and 18.75 g per hectare respectively or 49.5 and 22.5 g per hectare respectively. Alternatively, the imidazolinone may be used as a combination of imazapic and imazapyr at a rate of 26.25 and 8.75 g per hectare respectively or 42 and 14 g per hectare respectively.

The invention also relates to a method of growing a barley crop comprising sowing the seed of the invention and cultivating the seed and resultant plant under suitable conditions to produce a crop.

Preferably the herbicide resistant barley used for the crop is produced by mutagenesis, more preferably chemical mutagenesis.

Still more preferably the herbicide resistant crop is, or is derived from, NCIMB 41548, NCIMB 41549 or NCIMB 41550 or has the herbicide resistant characteristics thereof.

The following non limiting examples describe the invention.

Example 1

Production of Mutants 33.3 kg (approximately 812,195 seeds) of the barley variety Buloke was soaked in 0.25% Ethyl methane sulfonate (EMS) and dried using an air blower. The parent Buloke is a high yielding variety which produces grain of malting quality. Surprisingly Buloke is suited to areas where brome grass is a problem weed. In selecting this strain, the inventors hoped to develop an imidazolinone resistant barley variety which could be grown under conditions where brome grass and other weeds may be controlled with imidazolinone herbicides.

Example 2

M1 Generation

Mutated barley seed from Example 1 was sown in a plot of 0.5 ha at Horsham, Victoria, Australia in 2006. Management was consistent with those recommended for barley in the region. At maturity the plot was harvested by an experimental plot harvester. 300 g samples were taken from each full seed bin and bulked together to form a representative smaller composite (150 kg) and remaining seed was bulked together as a composite sample (600 kg).

Example 3

M2 Generation 200 kg of mutated barley seed from example 2 (approx. 4.88 million seeds) was sown on 2 ha of land at Horsham, Victoria, Australia in 2007. Emerged plants were sprayed with ON DUTY® at a rate of 80 g/ha (active ingredient Imazapic 42 g+Imazapyr 14 g) and 20 surviving plants were harvested individually by hand and retained.

Example 4

Preliminary Evaluation of M2 Selections for Resistance to Imidazolinone Herbicides The ten plants with the largest dry matter and seed yield from Example 3 were identified and designated BULOKE-EMS05*06HI001, BULOKE-EMS05*06HI002, BULOKE-EMS05*06HI003, BULOKE-EMS05*06HI004, BULOKE-EMS05*06HI005, BULOKE-EMS05*06HI006, BULOKE-EMS05*06HI007, BULOKE-EMS05*06H1008, BULOKE-EMS05*06HI009, BULOKE-EMS05*06HI010.

30 seeds from each selection were sown in 10 pots (3 seeds per pot) in a glasshouse. Half of the pots for each selection were sprayed with ON DUTY® at a rate of 50 g/ha (active ingredient Imazapic 26.25 g×Imazapyr 8.75 g) and each selection classified for resistance to ON DUTY® based on the reaction of progenies. Plants were deemed resistant if they appeared unaffected by ON DUTY® (no visual symptoms) or susceptible if they were killed by ON DUTY®, The following Homozygous susceptible (escapes in field screening) selections were identified and discontinued from further evaluation: BULOKE-EMS05*06HI001, BULOKE-EMS05*06HI004, BULOKE-EMS05*06HI1008.

The following Homozygous resistant selections were identified and resistant plants bulked together for evaluation: BULOKE-EMS05*06HI002, BULOKE-EMS05*06HI005, BULOKE-EMS05*06HI006, BULOKE-EMS05*06HI009, BULOKE-EMS05*06HI010.

Although homozygous for resistance to ON DUTY, BULOKE-EMS05*06HI009 was segregating for genes that affected plant type and single plants were harvested separately for further evaluation.

Heterozygous susceptible/resistant selections were identified and individual resistant plants were harvested for further evaluation: BULOKE-EMS05*06HI003, BULOKE-EMS05*06HI007

A homozygous herbicide resistant line representing each original resistant M2 plant selection was selected for submission to NCIMB and further evaluation. These lines were given shorter, new names to improve communications as shown in Table 2:

TABLE 2

| Name | Original name |
|---|---|
| VBHT0803 | BULOKE-EMS05*06HI003-06GI003 |
| VBHT0805 | BULOKE-EMS05*06HI005 |
| VBHT0806 | BULOKE-EMS05*06HI006 |
| VBHT0807 | BULOKE-EMS05*06HI007-06GI001 |
| VBHT0810 | BULOKE-EMS05*06HI010 |

Table 2: Original and new names for homozygous herbicide resistant lines

Example 5

Field Evaluation for Tolerance to Intervix® a) Selection of Lines with Homozygous Resistance to Imidazolinone Herbicides

Seed from single plants selected in the glasshouse (Example 4) were sown in 5 m paired rows at Horsham, Victoria, Australia, in 2007 and sprayed with 0.75 L/ha of Intervix® (active ingredient Imazamox 33 grams/kg+Imazapyr 15 grams/kg) post emergence and rows that were visually unaffected by the herbicide were harvested for further evaluation (data not presented). Homozygous imidazolinone resistant lines VBHT0803 and VBHT0806 were identified and submitted to NCIMB.

b) Evaluation of Resistance to Imidazolinone Herbicides

The imidazolinone resistance of the mutated lines VBHT0805, VBHT0806, and VBHT0810 were compared to the wild type lines Buloke and Hindmarsh in experiments at Horsham, Victoria, Australia in 2007 and 2008 and Marinna, NSW, Australia in 2008. At Horsham the experiments were sown in a split plot design with 2 replications in 2007 and 3 replications in 2008, and at Marinna a factorial design was used with 3 replications. At Horsham genotypes (Selections) were allocated as subplots and herbicide treatment as mainplots Herbicide treatments were:

Horsham 2007—no applied Intervix® and Intervix® applied post emergence at 0.75 L/ha (active ingredient 24.75 g imazamox+11.25 g imazapyr)

Horsham 2008—no applied Intervix® and Intervix® applied post emergence at 0.375 L/ha (active ingredient 12.375 g imazamox+5.625 g imazapyr), 0.75 L/ha (active ingredient 24.75 g imazamox+11.25 g imazapyr), 1.5 L/ha (active ingredient 49.5 g imazamox+22.5 g imazapyr).

Marinna 2008—no applied Intervix® and Intervix® applied post emergence at 0.375 L/ha (active ingredient 12.375 g imazamox+5.625 g imazapyr), 0.75 L/ha (active ingredient 24.75 g imazamox+11.25 g imazapyr), 1.25 L/ha (active ingredient 41.25 g imazamox+18.75 g imazapyr).

Management of all experiments was consistent with established commercial practices except the application of Intervix® herbicide. Plots were harvested using a small plot harvester, and seed weighed, converted to yield in t/ha and analyzed using REML. A 500 gram sample from replication 1, no applied Intervix® was evaluated for malting quality using established methods (see Example 10).

Intervix® applied at all rates significantly reduced the grain yield of the varieties Buloke and Hindmarsh compared to the control treatment (no applied Intervix) in all three experiments (Tables 3, 4 and 5). In both cases all plants in the Intervix® treated plots turned yellow, ceased to grow and died. In contrast, there was no significant difference in the grain yield of VBHT0805, VBHT0806 or VBHT0810 when treated with Intervix® at any rate compared to the control treatment (no applied Intervix). Furthermore, no visual symptoms of damage could be observed in the Intervix® treated plots of VBHT0805, VBHT0806 or VBHT0810. VBHT0805, VBHT0806 or VBHT0810 are all derived from Buloke that was treated with EMS and clearly exhibit improved resistance to Intervix® at rates from 0.375 L/ha (active ingredient 12.375 g imazamox+5.625 g imazapyr) to 1.5 L/ha (active ingredient 49.5 g imazamox+22.5 g imazapyr) compared to the wild type parent Buloke and the cultivar Hindmarsh.

Example 6

Field Evaluation to Compare the Yield of Imidazolinone Resistant Mutant Barley Lines with Buloke The yield (t/ha) of imidazolinone resistant mutant lines VBHT0805, VBHT0806 or VBHT0810 were compared with Buloke at 9 sites in Australia, Paskeville and Paskeville and Callington were located in the state of South Australia, Forbes, Temora and Junee Reefs in New South Wales, Dimboola, Elmore and Mt Mercer in Victoria, and Northam early and late sown in Western Australia.

VBHT0805 had the highest yields across all sites and averaged 4% higher than Buloke indicating that the mutation process had not cause deleterious mutations that significantly affect grain yield in Australia. Alternatively VBHT0806 was 4% lower yielding than Buloke. These results are shown in Table 6.

Example 7

Morphological and DNA Comparison of Imidazolinone Resistant Mutant Barley Lines with Buloke The morphological characteristics and DNA of imidazolinone resistant mutant barley lines VBHT0803, VBHT0805, VBHT0806, VBHT0807 and VBHT0810 were compared with the wild type Buloke. Table 7 describes the distinctive morphological and DNA characteristics identified. VBHT0803 differs from Buloke in having purple awns and is shorter than Buloke but not a dwarf.

VBHT0805, VBHT0807 and VBHT0810 have identical haplotypes suggestive of being derivatives of a single mutational event. VBHT0803 and VBHT0806 have unique haplotypes that is likely to be due to the heterogeneity within the original Buloke sample used for the mutagenesis and indicates that each represents a unique mutational event for resistance to imidazolinone herbicides. The haplotypes of VBHT0805, VBHT0807 and VBHT0810 differed from the Buloke reference sample (VB0105*12) at 41 of 1424 single polynucleotide polymorphism (SNP) loci.

Example 8

DNA Sequencing of the AHAS Gene of Imidazolinone Resistant Mutant Barley Lines a. Overview:

Mutant lines of barley (*Hordeum vulgare* L.) screened for resistance to the herbicide imidazolinone and identified as containing resistance determinants as per the previous examples were tested to confirm and characterise the mutant lines, the suspected mutant alleles of the acetohydroxyacid synthase (AHAS) gene, and resequenced to identify DNA base changes. The DNA sequences were collated and compared to wild type sequences and known mutations.

b. Experimental Approaches and Results:

The plant material consisted of the wild type genotypes, Buloke along with 3 mutant lines derived from Buloke numbered VBHT0805 (NCIMB 41549), VBHT0806 (NCIMB 41550) and VBHT0810 (not deposited). A collection of publicly available reference sequences of the AHAS gene was assembled from Genbank. The sequences were obtained from a range of monocotyledonous species, (including barley) and were used for PCR primer design to conserved regions of the gene to ensure optimal primer performance. A total of 20 primers were designed in forward and reverse orientation to enable maximal coverage of the available gene sequence and provide multiple options for primer pairing to mitigate the possibility of poor primer performance.

PCR amplification using standard conditions was tested on all supplied DNA templates. Amplification performance was low, with all possible primer combinations and resulted in the production of multiple products as resolved on an agarose gel. Nested PCR was employed to reduce amplification product complexity and to increase reaction specificity. Using the nested PCR strategy a region of the AHAS gene was uniquely amplified and was subjected to direct sequencing using Big-Dye 3.1 resolved on an Abi 3730x1. The sequences were then aligned using Sequencher v3.7 and assessed for polymorphism.

Several variant mutated bases were identified. At base coordinate 1431 line VBHT0810 has a transition from G to A. However, this change is unlikely to be causal for the observed phenotype of herbicide resistance as this specific nucleotide is the third base in the triplet codon and codes for the same amino acid and is therefore synonymous.

In lines VBHT0805 (NCIMB 41549) and VBHT0806 (NCIMB 41550) at base coordinate 1742 G has been mutated to A, also a transition. This causes alteration of the resulting amino acid from serine to asparagine (FIG. 1).

Using cross-species comparative analysis, the serine amino acid that has been mutated in lines VBHT0805 (NCIMB 4159) and VBHT0806 (NCIMB 41550) has been identified as being highly conserved in other species (FIG. 2).

Comparison of this serine to asparagine specific change to known causal mutations that confer plant herbicide resistance, conforms to previously identified and characterised changes (Li et al 2008; Jander et al. 2004; Sathasivan et al. 1990).

c. Conclusions:

Mutant lines VBHT0805 (NCIMB 41549) and VBHT0806 (NCIMB 41550) are likely to express herbicide resistance due to alteration of coordinate 1742 changing from a G to an A, which alters the amino acid from a serine to an asparagine. This mutation is referred to as SER653. The imidazolinone herbicide resistance shown in the barley of the present invention is surprisingly high compared to levels found in other species. This was unexpected and while not wishing to be bound by theory it may be possibly due to the high copy number of the AHAS gene in barley.

Example 9

Further Sequencing Work

Further work was being carried out using standard sequencing techniques similar to those of Example 8 to characterise the AHAS gene and other possibly relevant genes involved in conferring imidazolinone resistance in VBHT0803 (NCIMB 41548), VBHT0805 (NCIMB 41549), VBHT0806 (NCIMB 41550), VBHT0807 and VBHT0810.

VBHT0803 (NCIMB 41548) was found to have the SER 653 mutation.

VBHT0807 and VBHT0810 (not deposited) were found to have the SER 653 mutation.

Example 10

Suitability for Malt Production

Buloke is currently recognised as a malting cultivar in Australia. Tests for suitability for malt production were carried out in accordance with the standard procedures of the European Brewing Congress. The results shown in Table 8 demonstrate that VBHT0805 (NCIMB 41549) is equivalent to Buloke in its suitability for malting.

Example 11

Production of Herbicide Resistant Derivates of VBHT0805 via Backcrossing with Hindmarsh The imidazolinone resistance from VBHT0805 has been transferred through backcrossing to derivatives of the high yielding dwarf barley variety Hindmarsh that is susceptible to imidazolinone herbicides. Lines from these crosses have been identified that retain the characteristics of Hindmarsh, including dwarf growth habit, but also have resistance to imidazolinone herbicides that is comparable to VBHT0805. Hindmarsh is genetically different and unrelated to Buloke, the original line used to develop VBHT0805, and these findings indicate that the imidazolinone resistance discovered and outlined in the above examples can be transferred to progeny and are thus derivatives of VBHT0805.

TABLE 1

Deposits

| Designation | Accession No. |
|---|---|
| VBHT 0803 | NCIMB 41548 |
| VBHT 0805 | NCIMB 41549 |
| VBHT 0806 | NCIMB 41550 |

The strains were deposited under conditions that assure that access to the culture will be available during the pendency of this patent application to one determined by foreign patent laws to be entitled thereto. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

In a preferred embodiment the seeds of the invention are VBHT 0803, VBHT 0805 or VBHT 0806 as described herein or are plants derived from these seeds. The invention also provides seeds or plants which are mutants, derivatives and variants thereof having increased imidazolinone resistance compared to wild type barley plants. The plants derived from these seeds may have barley plant cells expressing proteins encoded by a nucleic acid sequence depicted in SEQ ID NO: 1, SEQ ID NO: 2, or SEQ ID NO: 3, or a derivative thereof. Alternatively, the plants derived from these seeds may have barley plant cells expressing a protein comprising an amino acid sequence depicted in SEQ ID NO:4. SEQ ID NO: 1 to 4 are illustrated below, the four sequences being:

SEQ ID 1 is for the NCIMB 41549 deposit (applicant's ID: VBHT 0805) and is the same as that given in FIG. 3.

SEQ ID 2 is for the NCIMB 41550 deposit (applicant's ID: VBHT 0806) and is the same as that given in FIG. 3.

SEQ ID 3 is for the NCIMB 41548 deposit (applicant's ID: VBHT 0803) and has the same mutation as ID 1 and 2, and confirmed in Example 9.

SEQ ID 4 is the amino sequence given in FIG. 2 for the "mutant" line

The sequence listing contained in this application is submitted herewith by EFS-WEB in the form of a text file.

REFERENCES

Li D., Barclaya I., Jose K., Stefanova K., Appels R. 2008. A mutation at the Ala122 position of acetohydroxyacid synthase (AHAS) located on chromosome 6D of wheat; improved resistance to imidazolinone and a faster assay for marker selection. Mol Breeding. Published Online early.

Jander G., Baerson S., Hudak J., Gonzalez K., Gruys K., Last R. 2003 Ethylmethanesulfonate Saturation Mutagenesis in Arabidopsis to Determine Frequency of Herbicide Resistance. Plant Physiology 131 p139-16.

Sathasivan K., Haughn G., Murai N. 1990 Nucleotide sequence of a mutant acetolactate synthase gone from an imidazolinone-resistant Arabidopsis thaliena var. Columbia. Nucleic Acids Research 18 2188.

The invention claimed is:

1. A non-naturally occurring barley plant with increased resistance to imidazolinone herbicides compared to a wild type Buloke barley plant and deposited under NCIMB Deposit accession number NCIMB 41548 or NCIMB 41549.

2. A seed of the plant of claim 1, said seed having increased resistance to imadazolinone herbicides compared to seed of a wild type Buloke barley plant.

3. A method of inhibiting weed growth in the vicinity of a barley plant comprising growing the barley plant of claim 1 and applying imidazolinone herbicide to said barley plant and its vicinity sufficient to inhibit weed growth.

4. The method of claim 3 wherein the imidazolinone herbicide used is a combination of imazamox and imazapyr applied post emergence at a rate of 12.375 g per hectare and 5.625 g per hectare respectively; 24.75 and 11.25 g per hectare respectively; 41.25 and 18.75 g per hectare respectively or 49.5 and 22.5 g per hectare respectively.

5. The method of claim 3 wherein wherein the imidazolinone herbicide used is a combination of imazamox and imazapyr applied at a rate of 26.25 and 8.75 g per hectare respectively or 42 and 14 g per hectare respectively.

6. A method of growing a barley crop comprising the steps of:

sowing the seed of claim 2; and
cultivating said seed and a plant resulting therefrom to produce a barley crop.

7. The method of claim 6 further comprising a step of applying an imidazolinone herbicide to said crop to inhibit growth of weeds in the crop.

8. The method of claim 3, wherein the imidazolinone herbicide comprises at least two constituents selected from the group consisting of imazamox, imazapyr, and imazapic.

9. The method of claim 3 wherein said imidazolinone herbicide is applied after plant emergence.

10. The method of claim 4 wherein the imazamox and imazapyr are applied at a rate of 12.375 g per hectare and 5.625 g per hectare respectively; 24.75 and 11.25 g per hectare respectively 41.25 and 18.75 g per hectare respectively or 49.5 and 22.5 g per hectare respectively.

11. The method of claim 5 wherein the imazapic and imazapyr are applied at a rate of 26.25 and 8.75 g per hectare respectively or 42 and 14 g per hectare respectively.

12. The non-naturally occurring barley plant of claim 1, deposited as NCIMB Deposit accession number NCIMB 41548.

13. The non-naturally occurring barley plant of claim 1, deposited as NCIMB Deposit accession number NCIMB 41549.

* * * * *